(12) United States Patent
Yeh et al.

(10) Patent No.: US 9,872,882 B2
(45) Date of Patent: Jan. 23, 2018

(54) AURANTIAMIDE DIPEPTIDE DERIVATIVES FOR TREATMENT OR PREVENTION OF ANGIOGENESIS-RELATED DISEASES

(71) Applicants: Mackay Medical College, New Taipei (TW); MacKay Memorial Hospital of Taiwan Presbyterian Church and MacKay Memorial Social Work Foundation, Taipei (TW); Chang Gung University, Taoyuan (TW)

(72) Inventors: Hung-I Yeh, Taipei (TW); Shih-Wei Wang, New Taipei (TW); Ching-Hu Chung, New Taipei (TW); Pei-Wen Hsieh, Taoyuan (TW)

(73) Assignees: MACKAY MEDICAL COLLEGE, New Taipei (TW); MACKAY MEDICAL FOUNDATION THE PRESBYTERIAN CHURCH IN TAIWAN MACKAY MEMORIAL HOSPITAL, Taipei (TW); CHANG GUNG UNIVERSITY, Taoyuan (TW)

( * ) Notice: Subject to any disclaimer, the term of this patent is extended or adjusted under 35 U.S.C. 154(b) by 0 days.

(21) Appl. No.: 14/981,178

(22) Filed: Dec. 28, 2015

(65) Prior Publication Data
US 2017/0182114 A1  Jun. 29, 2017

(51) Int. Cl.
*A61K 38/05* (2006.01)
*A61K 45/06* (2006.01)

(52) U.S. Cl.
CPC .............. *A61K 38/05* (2013.01); *A61K 45/06* (2013.01); *G01N 2800/7014* (2013.01); *G01N 2800/7028* (2013.01); *G01N 2800/7042* (2013.01)

(58) Field of Classification Search
None
See application file for complete search history.

(56) References Cited

PUBLICATIONS

Office action dated Nov. 28, 2016 by the Taiwan Intellectual Property Office (TIPO) for corresponding Taiwan application No. 104143726.
English abstract translation of the office action dated Nov. 28, 2016 by the Taiwan Intellectual Property Office (TIPO) for corresponding Taiwan application No. 104143726.
Yen, Chia-Ting et al,. European Journal of Medicinal Chemistry, vol. 45(6), Jun. 2010 pp. 1494-2502.

*Primary Examiner* — Satyanarayana R Gudibande
*Assistant Examiner* — Jia-Hai Lee
(74) *Attorney, Agent, or Firm* — WPAT, P.C.; Anthony King

(57) ABSTRACT

The invention relates to a use of an aurantiamide dipepetide derivative in the treatment or prevention of angiogenesis-related diseases. Accordingly, aurantiamide dipeptide derivatives can be used as angiogenesis inhibitor, whereby preventing or treating invasive and metastatic cancer and ocular neovascularization (particularly macular degeneration such as pathological neovascularization of age-related macular degeneration (AMD)).

10 Claims, 11 Drawing Sheets

Fig. 1A Fomc-10a
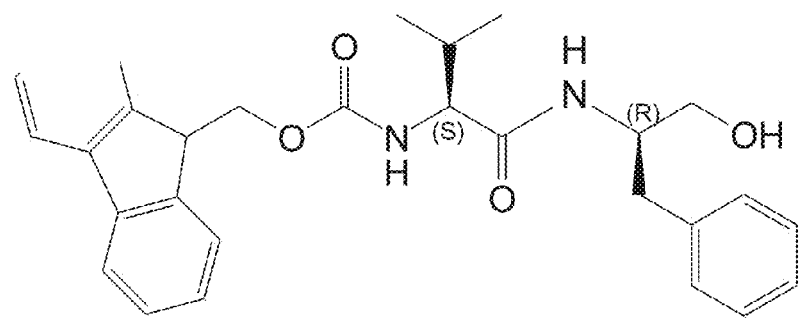
Fig. 1B
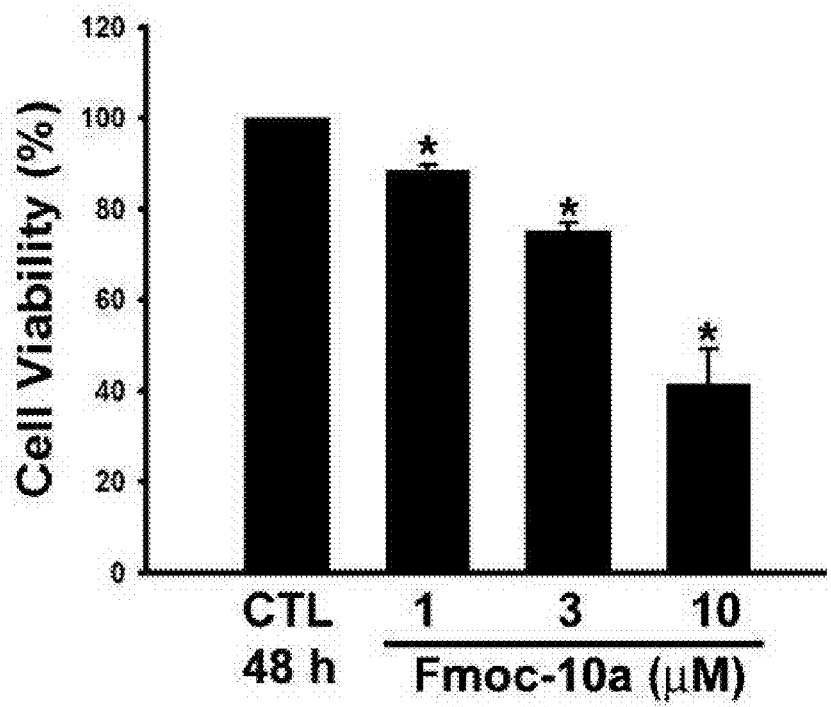

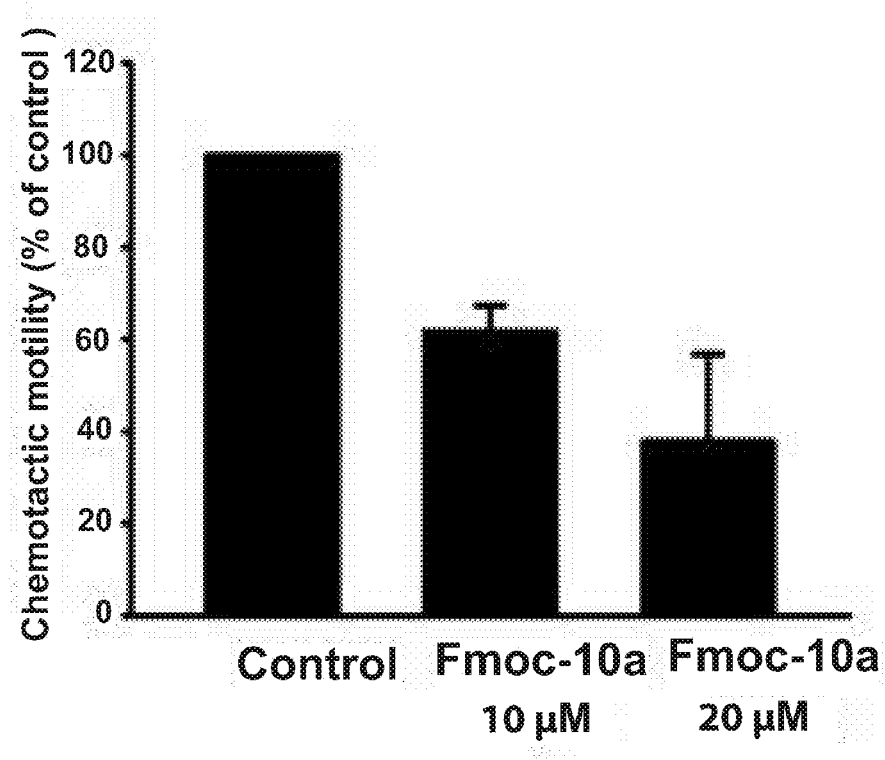

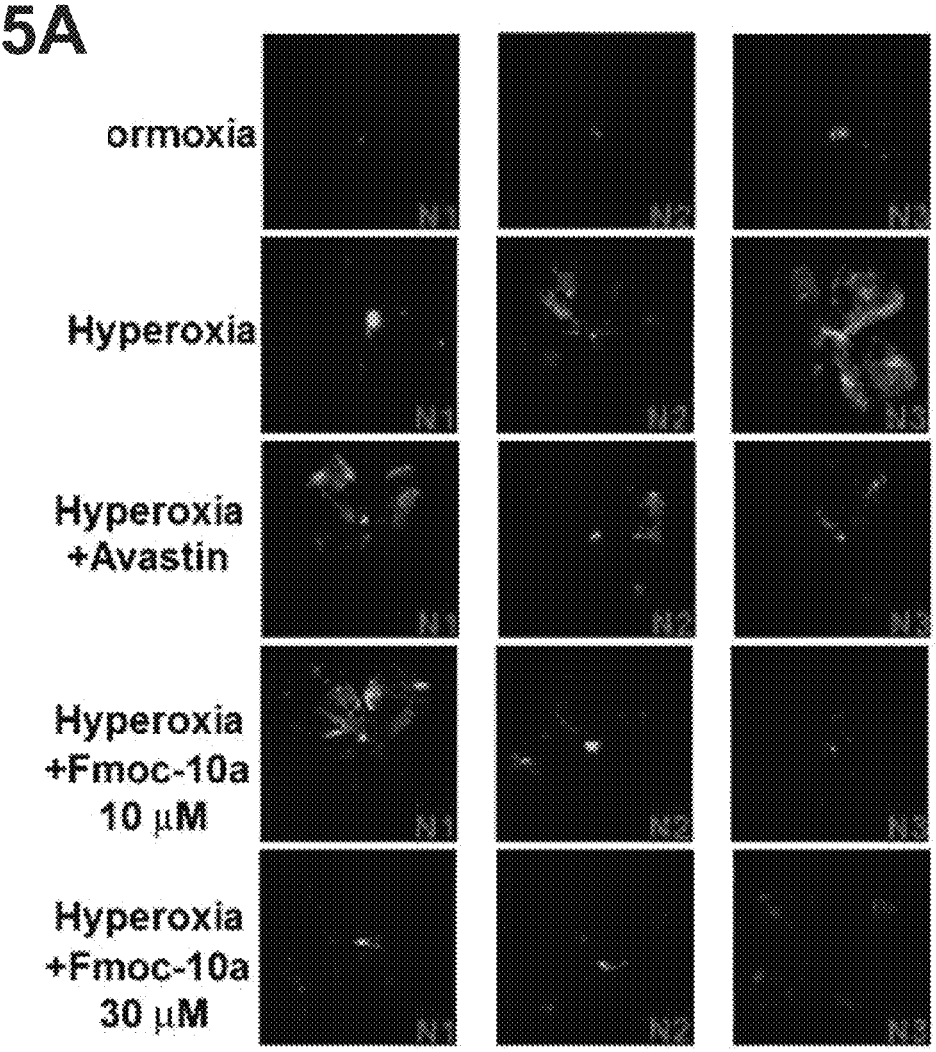

US 9,872,882 B2

AURANTIAMIDE DIPEPTIDE DERIVATIVES FOR TREATMENT OR PREVENTION OF ANGIOGENESIS-RELATED DISEASES

FIELD OF THE INVENTION

The invention is directed to treatment or prevention of angiogenesis-related diseases. Particularly, the invention relates to use of an aurantiamide dipeptide derivative in the treatment or prevention of angiogenesis-related diseases.

BACKGROUND OF THE INVENTION

Angiogenesis plays a critical role in physiological conditions such as embryonic development, reproduction, tissue repair and bone remodeling. In contrast, angiogenesis is recognized as a common denominator underlying a variety of deadly and debilitating human diseases, including cancer, age-related macular degeneration (AMD) and various inflammatory diseases. Tumor angiogenesis has been demonstrated to facilitate cancer progression and metastasis in the microenvironment. Pathological angiogenesis is also the major cause of AMD, which is one of the most common irreversible causes of severe loss of vision in the elderly population. Neovascular-AMD is characterized by choroidal neovascularization (CNV) that invades the subretinal space, often leading to exudation and hemorrhage.

Neovascularization involves recruitment of circulating endothelial progenitor cells (EPCs) from bone marrow to hypoxia sites as well as sprouting of preexisting endothelial cells. EPCs are a population of cells in the circulation and carry out angiogenesis and vascular remodeling for their ability to differentiate into endothelia cells and form blood vessels. Late EPCs have merits of being more committed to endothelial lineage differentiation and contribute to angiogenesis. Moreover, early EPCs have been proposed to improve angiogenesis/vasculogenesis through the production of angiogenic cytokines (e.g. VEGF and IL-8), which might activate adjacent endothelial cells. Recently, EPCs reportedly mediate early tumor growth and late metastatic progression by intervening with the angiogenic switch. Accumulated evidences indicate that EPCs promote the neovascularization in ischemic hypoxia tissue during AMD. These findings establish the role of EPCs in pathological angiogenesis and support that EPC targeting therapies may be the promising strategy to block angiogenesis-related diseases.

Dipeptide dertivative Fmoc-10a (9H-fluoren-9-yl)methyl (S)-1-((R)-1-hydroxy-3-phenylpropan-2-ylamino)-3-methyl-1-oxobutan-2-ylcarbamate) is an aurantiamide derivative, which composed of phenylalaninol and phenylalanine, and were a major component of *Zanthoxylum dissitum, Semiaquilegia adoxoides* and *Polygonum chinensis*. Aurantiamides exhibited anti-bacterial, anti-inflammatory (Chiao-Ting Yen et al., European Journal of Medicinal Chemistry 44 (2009) 1933-1940), antioxidant, and anti-HIV effects. Recently, many dipeptides showed cytotoxic effects against cancer cells (Chiao-Ting Yen et al., European Journal of Medicinal Chemistry 45 (2010) 2494-2502). For example, Peptichemio (PTC) and Bortezomib (VELCADE®) were developed and marketed for treating cancer.

SUMMARY OF THE INVENTION

The invention provides a method for inhibiting, ameliorating, preventing or treating an angiogenesis-related disease, comprising administering an effective amount of a compound of Formula (I) described herein or a tautomer, stereoisomer or enantiomer thereof, or a solvate, prodrug or a pharmaceutically acceptable salt thereof to a subject.

In some embodiments, the compound of formula (I) is selected from (9H-Fluoren-9-yl)methyl(S)-1-((S)-1-hydroxy-3-phenylpropan-2-ylamino)-1-oxo-3-phenylpropan-2-ylcarbamate; (9H-Fluoren-9-yl)methyl(S)-1-((R)-1-hydroxy-3-phenylpropan-2-ylamino)-1-oxo-3-phenylpropan-2-ylcarbamate; (9H-Fluoren-9-yl)methyl(S)-1-((S)-1-hydroxy-3-phenylpropan-2-ylamino)-3-(1H-indol-3-yl)-1-oxopropan-2-ylcarbamate; (9H-Fluoren-9-yl)methyl(S)-1-((R)-1-hydroxy-3-phenylpropan-2-ylamino)-3-(1H-indol-3-yl)-1-oxopropan-2-ylcarbamate; (9H-Fluoren-9-yl)methyl(S)-1-((S)-1-hydroxy-3-phenylpropan-2-ylamino)-3-(naphthalen-2-yl)-1-oxopropan-2-ylcarbamate; (9H-Fluoren-9-yl)methyl(S)-1-((R)-1-hydroxy-3-phenylpropan-2-ylamino)-3-(naphthalen-2-yl)-1-oxopropan-2-ylcarbamate; (9H-Fluoren-9-yl)methyl(S)-1-((S)-1-hydroxy-3-phenylpropan-2-ylamino)-3-methyl-1-oxobutan-2-ylcarbamate; and (9H-Fluoren-9-yl)methyl(S)-1-((R)-1-hydroxy-3-phenylpropan-2-ylamino)-3-methyl-1-oxobutan-2-ylcarbamate; or a tautomer, stereoisomer or enantiomer thereof, or a solvate, prodrug or a pharmaceutically acceptable salt thereof. In a further embodiment, the compound is (9H-fluoren-9-yl)methyl(S)-1-((R)-1-hydroxy-3-phenylpropan-2-ylamino)-3-methyl-1-oxobutan-2-ylcarbamate.

In one embodiment, the angiogenesis-related disease is an invasive and metastatic angiogenesis-related cancer or ocular neovascularization.

In some embodiments, the invasive and metastatic angiogenesis-related cancer include, but is not limited to, oral cancer, brain cancer, breast cancer, renal cancer, ovarian cancer, lung cancer, colon cancer, liver cancer (such as hepatocellular carcinoma) and melanoma. In a further embodiment, the invasive and metastatic angiogenesis-related cancer is melanoma. In some embodiments, for the invasive and metastatic angiogenesis-related cancer, the administration can be employed in combination with, prior to or subsequently to, surgery, radiotherapy or chemotherapy.

In one embodiment, the ocular neovascularization is macular degeneration. Preferably, the macular degeneration is wet macular degeneration. More preferably, the wet macular degeneration is AMD. In one embodiment, for macular degeneration, the administration is in an as an injection or eye drop.

BRIEF DESCRIPTION OF THE DRAWING

FIGS. 1A to 1E show that Fmoc-10a inhibits angiogenic effects of late EPCs. FIG. 1A chemical structure of Fmoc-10a. FIG. 1B Fmoc-10a inhibited cell growth of late EPCs in a concentration-dependent manner using MTT assay. FIG. 1C Fmoc-10a did not induce LDH release in late EPCs using LDH assay. FIG. 1D Fmoc-10a suppressed cell migration of late EPCs using Transwell migration assay. FIG. 1E Fmoc-10a abolished capillary tube-like structure of late EPCs using tube formation assay. Data are expressed as mean±SEM of five independent experiments. *, p<0.01 compared with control group.

FIGS. 2A and 2B Fmoc-10a inhibited colony-forming units (CFUs) of early EPCs using CFU-Hill assay. FIG. 2C Fmoc-10a suppressed chemotaxis of early EPCs using chemotactic motility assay. Data are expressed as mean±SEM of four independent experiments.

FIG. 3A Fmoc-10a abrogated VEGF-induced vessels sprouting using aortic ring sprouting assay. FIG. 3B Fmoc-10a attenuated VEGF-induced microvessel formation using in vivo mouse DIVAA model. Data are expressed as mean±SEM of three independent experiments. *, p<0.01 and **, p<0.001 compared with vehicle group.

FIG. 4A Fmoc-10a significantly inhibited cell invasion of B16F10 melanoma cells. FIG. 4B Fmoc-10a concentration-dependently suppressed VEGF release from B16F10 melanoma cells. FIG. 4C Fmoc-10a induced a dose-dependent inhibition of B16F10 melanoma growth using tumor xenograft model. FIG. 4D, Fmoc-10a inhibited pulmonary colony number of B16F10 cells using experimental metastasis model. Data are expressed as mean±S.E.M. of three independent experiments. *, p<0.05, , p<0.01 and *, p<0.001 compared with vehicle group.

FIGS. 5A and 5B show that Fmoc-10a inhibits the choroidal neovascularization (CNV) in AMD animal model. FIG. 5A The mouse model of oxygen-induced retinopathy (OIR) was performed to induce retinal neovascularization in 7 day-old mice under hyperoxia condition. Whole-mount analysis of retinal neovascularization showed hyperoxia dramatically increased the fluorescence of isolectin. Fmoc-10a significantly blocked hyperoxia-induced pathological neovascularization in mice, and Avastin (10 µg) was used as positive control. FIG. 5B The quantitative detection of neovascularization in retina was represented from four independent experiments. Data are expressed as the mean±S. E. *, p<0.001 compared with normoxia group; #, p<0.05 compared with vehicle-treated group under hyperoxia.

DETAILED DESCRIPTION OF THE INVENTION

Figure 1C:
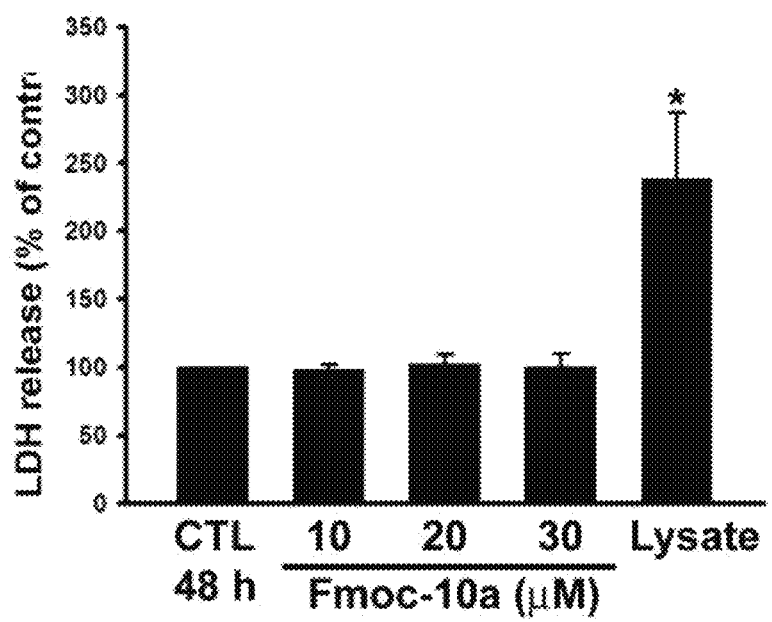

The invention is based, at least in part, on the discovery of aurantiamide dipeptide derivatives in the inhibition of angiogenesis. Accordingly, aurantiamide dipeptide derivatives can be used as angiogenesis inhibitor, whereby preventing or treating invasive and metastatic angiogenesis-related cancer (particularly metastasis of melanoma) and ocular neovascularization (particularly macular degeneration such as pathological neovascularization of age-related macular degeneration (AMD)).

For convenience, certain terms employed in the context of the present disclosure are collected here. Unless defined otherwise, all technical and scientific terms used herein have the same meaning as commonly understood by one of the ordinary skill in the art to which this invention belongs.

The singular forms "a," "an," and "the" are used herein to include plural referents unless the context clearly dictates otherwise.

The term "treatment" or treating as used herein is intended to mean obtaining a desired pharmacological and/or physiologic effect, e.g., ameliorating the symptoms associated with a disease. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered," "administering" or "administration" are used interchangeably herein to refer a mode of delivery, including, without limitation, intravenously, intramuscularly, intraperitoneally, intraarterially, subcutaneously, or transdermally administering an agent (e.g., compound or a composition) of the present invention.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of a compound or an antibody or dosage form provided herein, with or without one or more other additional active agent(s), prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment.

As used herein, the terms "co-administration" and "in combination with" include the administration of two or more therapeutic agents simultaneously, concurrently or sequentially within no specific time limits unless otherwise indicated.

The term "an effective amount" as used herein refers to an amount effective at a certain dosage and period of time to achieve the desired result with respect to the treatment of a disease. An effective amount of an agent is not required to cure a disease or condition but will provide a treatment for a disease or condition such that the onset of the disease or condition is delayed, hindered or prevented, or the disease or condition symptoms are ameliorated. The effective amount may be a single dose or divided into two or more doses in a suitable form to be administered at one, two or more times throughout a designated time period.

The term "subject" or "patient" as used herein refers to an animal, including the human species, that is treatable with the method of the present invention. The term "subject" or "patient" is intended to refer to both the male and female gender unless one gender is specifically indicated. Accordingly, the term "subject" or "patient" comprises any mammal which may benefit from the treatment method of the present disclosure.

The term "angiogenesis-related disease" as used herein refers to a disorder characterized by pathological angiogenesis. A disorder characterized by pathological angiogenesis refers to a disorder where abnormal or aberrant angiogenesis, alone or in combination with others, contributes to causation, origination, or symptom of the disorder.

The term "combination therapy" as used herein refers to those situations in which two or more different pharmaceutical agents are administered in overlapping regimens so that the subject is simultaneously exposed to both agents.

The term "inhibit" as used herein means to prevent something from happening, to delay occurrence of something happening, and/or to reduce the extent or likelihood of something happening. Thus, "inhibiting angiogenesis" and "inhibiting the formation of neovasculature" is intended to encompass preventing, delaying, and/or reducing the likelihood of angiogenesis occurring as well as reducing the number, growth rate, size, etc., of neovessels.

The term "macular degeneration" as used herein refers to a medical condition that results in loss of vision in the center of the visual field (the macula) because of damage to the retina. "Wet macular degeneration" (also known as the neovascular or exudative form) refers to macular degeneration that involves the growth of blood vessels from the choroid behind the retina. In wet macular degeneration, the retina may sometimes become detached. "Age-related macular degeneration" (ARD) refers to the most common form of macular degeneration, which typically begins later in life with characteristic yellow deposits in the macula.

As used herein, the term "metastasis" (sometimes abbreviated as "mets;" plural "metastases") refers to the spread of tumor cells from one organ or tissue to another location. The term also refers to tumor tissue that forms in a new location as a result of metastasis. A "metastatic cancer" is a cancer that spreads from its original, or primary, location, and may also be referred to as a "secondary cancer" or "secondary tumor." Generally, metastatic tumors are named for the tissue of the primary tumor from which they originate.

The term "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

In one aspect, the invention provides a method for inhibiting, ameliorating, preventing or treating an angiogenesis-related disease, comprising administering an effective amount of a compound of the following Formula (I) to a subject,

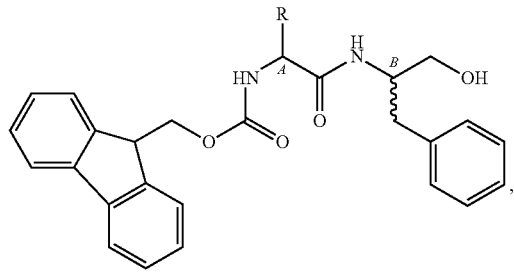

wherein R is —(CH$_2$)$_{1-4}$phenyl wherein phenyl is unsubstituted or substituted by one to three hydroxy, NH$_2$, NO$_2$ or alkyl; —(CH$_2$)$_{1-4}$indolyl; —(CH$_2$)$_{1-4}$-naphthalenyl; or isopropyl, or a tautomer, stereoisomer or enantiomer thereof, or a solvate, prodrug or a pharmaceutically acceptable salt thereof.

In some embodiments, R is —CH$_2$phenyl, —CH$_2$indolyl, —CH$_2$naphthalenyl or isopropyl. In a further embodiment, R is isopropyl.

In some embodiments, the compound of formula (I) is selected from:
(9H-Fluoren-9-yl)methyl(S)-1-((S)-1-hydroxy-3-phenyl-propan-2-ylamino)-1-oxo-3-phenylpropan-2-ylcarbamate;
(9H-Fluoren-9-yl)methyl(S)-1-((R)-1-hydroxy-3-phenyl-propan-2-ylamino)-1-oxo-3-phenylpropan-2-ylcarbamate;
(9H-Fluoren-9-yl)methyl(S)-1-((S)-1-hydroxy-3-phenyl-propan-2-ylamino)-3-(1H-indol-3-yl)-1-oxopropan-2-ylcarbamate;
(9H-Fluoren-9-yl)methyl(S)-1-((R)-1-hydroxy-3-phenyl-propan-2-ylamino)-3-(1H-indol-3-yl)-1-oxopropan-2-ylcarbamate;
(9H-Fluoren-9-yl)methyl(S)-1-((S)-1-hydroxy-3-phenyl-propan-2-ylamino)-3-(naphthalen-2-yl)-1-oxopropan-2-ylcarbamate;
(9H-Fluoren-9-yl)methyl(S)-1-((R)-1-hydroxy-3-phenyl-propan-2-ylamino)-3-(naphthalen-2-yl)-1-oxopropan-2-ylcarbamate;
(9H-Fluoren-9-yl)methyl(S)-1-((S)-1-hydroxy-3-phenyl-propan-2-ylamino)-3-methyl-1-oxobutan-2-ylcarbamate; and
(9H-Fluoren-9-yl)methyl(S)-1-((R)-1-hydroxy-3-phenyl-propan-2-ylamino)-3-methyl-1-oxobutan-2-ylcarbamate
or a tautomer, stereoisomer or enantiomer thereof, or a solvate, prodrug or a pharmaceutically acceptable salt thereof.

In a further embodiment, the compound is (9H-fluoren-9-yl)methyl(S)-1-((R)-1-hydroxy-3-phenylpropan-2-ylamino)-3-methyl-1-oxobutan-2-ylcarbamate. The chemical structure of the compound is

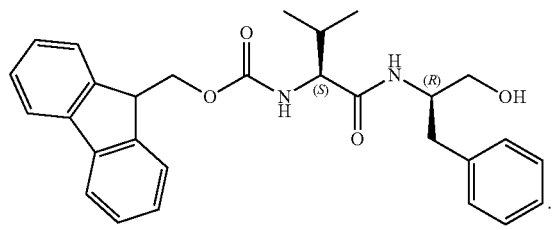

Angiogenesis involves the growth or sprouting of new microvessels from pre-existing vasculature, and vasculogenesis, which involves de novo vascular growth, is essential to many physiological and pathological conditions, including embryogenesis, invasive and metastatic cancer, rheumatoid arthritis, diabetic retinopathy, obesity, atherosclerosis, ischemic heart and limb disease, and wound healing. Over 70 diseases have been identified as angiogenesis dependent (Carmeliet, Nature, 438:932-6, 2005). Abnormal development of new blood vessels has been implicated in numerous pathophysiological processes. For example, abnormal growth of blood vessels is associated with bowel atresia, peptic ulcers, rheumatoid arthritis, systemic lupus erythematosus, psoriasis, proliferative retinopathy and atherosclerosis. As angiogenesis is involved in a variety of pathologic processes, inventive methods may be useful in treating, ameliorating or preventing diseases such as, for example invasive and metastatic cancer and ocular neovascularization (such as macular degeneration).

In some embodiments, the invasive and metastatic cancer is angiogenesis-related cancer. According to some embodiments, the invasive and metastatic angiogenesis-related cancer include, but is not limited to, oral cancer, brain cancer, breast cancer, renal cancer, ovarian cancer, lung cancer, colon cancer, liver cancer, hepatocellular carcinoma and melanoma.

In one embodiment, the ocular neovascularization is macular degeneration. The macular degeneration is the leading cause of vision loss and blindness in people aged 65 and older. Macular degeneration typically occurs in the age-related form (often called AMD), though juvenile macular degeneration occurs as well. In AMD, the macula—the part of the retina that is responsible for sharp, central vision—degenerates.

Wet macular degeneration, as the "neovascular" designation suggests, is characterized by new blood vessels growing aberrantly, e.g., on the macula. Such new blood vessels may grow beneath the retina, leaking blood and fluid. Such leakage causes permanent damage to light-sensitive retinal cells, which die and create blind spots in central vision. Wet macular degeneration may be further grouped into two categories. In the occult form of wet macular degeneration, new blood vessel growth beneath the retina is not as pronounced and leakage is less evident, typically resulting in less severe vision less. In the classic form of wet macular degeneration, blood vessel growth and scarring have very clear, delineated outlines that are observable beneath the retina. Classic wet macular degeneration is also known as classic choroidal neovascularization and usually results in more severe vision loss.

Given the role of angiogenesis in wet macular degeneration, which comprises many AMD cases, inventive methods may be useful in treating and/or preventing such disorders. Current therapies for wet macular degeneration involve angiogenesis inhibitors, optionally combined with photodynamic therapy (PDT) to target drugs to specific cells. Photocoagulation, in which a high energy laser beam is used to create small burns in areas of the retina with abnormal blood vessels, is also used to treat wet macular degeneration.

The compound of the invention may be administered to a mammal, preferably human, by any route that may effectively transport the compound or composition of the invention to the appropriate or desired site of action, such as oral, nasal, pulmonary, transdermal, such as passive or iontophoretic delivery, or parenteral, e.g., rectal, depot, subcutaneous, intravenous, intramuscular, intranasal, intra-cerebella, ophthalmic solution or ointment. A dosing regimen according to the present invention may consist of a single dose or a plurality of doses over a period of time. Administration may be one or multiple times daily, weekly (or at some other multiple day interval) or on an intermittent schedule. The exact amount of a compound described herein, or pharmaceutical composition thereof, to be administered will vary from subject to subject.

It may be desirable to reduce extent of angiogenesis in ocular neovascularization diseases. In some embodiments, the compound described herein may be delivered to the eye. Delivery to the eye may be achieved, for example, using intravitreal, intraocular and/or periocular routes such as intravitreal injection, subconjunctival injection, etc. Topical application of the compound described herein to the eye may also be achieved, for example, using eye drops. Ocular routes of administration may be particularly useful for treatment of ocular neovascularization diseases such as macular degeneration.

Depending on the route of administration, effective doses may be calculated according to the body weight; body surface area; primary organ/tumor size; and/or number, sizes, and/or types of metastases of the subject to be treated. The final dosage regimen will be determined by the attending physician, considering various factors which modify the action of the drugs, e.g., the drug's specific activity, the severity of the damage and the responsiveness of the patient, the age, condition, body weight, sex and diet of the patient, the severity of any present infection, time of administration, the use (or not) of other therapies, and other clinical factors.

The methods of the present invention can be employed in combination with additional therapies (i.e., a treatment according to the present invention can be administered concurrently with, prior to, or subsequently to one or more desired therapeutics or medical procedures). The particular combination of therapies (therapeutics or procedures) to employ in such a combination regimen will take into account compatibility of the desired therapeutics and/or procedures and the desired therapeutic effect to be achieved.

For example, for invasive and metastatic cancer, methods of the present invention can be employed together with other procedures including surgery, radiotherapy (e.g., gamma-radiation, neuron beam radiotherapy, electron beam radiotherapy, proton therapy, brachytherapy, systemic radioactive isotopes), chemotherapy, endocrine therapy, hyperthermia, and cryotherapy, depending on the tumor to be treated.

Methods of the present invention can also be employed concurrently, separately or subsequently with one or more further combinations of a second anticancer agent. The second anticancer agent includes, but is not limited to, an antimetabolite (e.g., 5-fluoro uracil, methotrexate, fludarabine, cytarabine (also known as cytosine arabinoside or Ara-C), and high dose cytarabine), antimicrotubule agent (e.g., vinca alkaloids, such as vincristine and vinblastine; and taxane, such as paclitaxel and docetaxel), alkylating agent (e.g., mechlorethamine, chlorambucil, cyclophosphamide, melphalan, melphalan, ifosfamide, carmustine, azacitidine, decitabine, busulfan, cyclophosphamide, dacarbazine, ifosfamide, and nitrosoureas, such as carmustine, lomustine, bischloroethylnitrosurea, and hydroxyurea), platinum agent (e.g., cisplatin, carboplatin, oxaliplatin, satraplatin (JM-216), and CI-973), anthracycline (e.g., doxorubicin and daunorubicin), antitumor antibiotic (e.g., mitomycin, bleomycin, idarubicin, adriamycin, daunomycin (also known as daunorubicin, rubidomycin, or cerubidine), and mitoxantrone), topoisomerase inhibitor (e.g., etoposide and camptothecin), purine antagonist or pyrimidine antagonist (e.g., 6-mercaptopurine, 5-fluorouracil, cytarabine, clofarabine, and gemcitabine), cell maturing agent (e.g., arsenic trioxide and tretinoin), DNA repair enzyme inhibitor (e.g., podophyllotoxine, etoposide, irinotecan, topotecan, and teniposide), enzyme that prevents cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormone (e.g., dexamethasone, prednisone, methylprednisolone, tamoxifen, leuprolide, flutamide, and megestrol), monoclonal antibody (e.g., gemtuzumab ozogamicin, alemtuzumab, rituximab, and yttrium-90-ibritumomab tiuxetan), immuno-modulator (e.g., thalidomide and lenalidomide), Bcr-Abl kinase inhibitor (e.g., AP23464, AZD0530, CGP76030, PD180970, SKI-606, imatinib, BMS354825 (dasatinib), AMN107 (nilotinib), and VX-680), hormone agonist or antagonist, partial agonist or partial antagonist, kinase inhibitor, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, and agents to attenuate any adverse effect (e.g., antiemetics). In one embodiment, the anticancer agent or cancer therapeutic agent is a cytotoxic agent, an anti-metabolite, an antifolate, an HDAC inhibitor, a DNA intercalating agent, a DNA cross-linking agent, a DNA alkylating agent, a DNA cleaving agent, a topoisomerase inhibitor, a CDK inhibitor, a JAK inhibitor, an anti-angiogenic agent, a Bcr-Abl inhibitor, an HER2 inhibitor, an EGFR inhibitor, a VEGFR inhibitor, a PDGFR inhibitor, an HGFR inhibitor, an IGFR inhibitor, a c-Kit inhibitor, a Ras pathway inhibitor, a PI3K inhibitor, a multi-targeted kinase inhibitor, an mTOR inhibitor, an anti-estrogen, an anti-androgen, an aromatase inhibitor, a somatostatin analog, an ER modulator, an anti-tubulin agent, a vinca alkaloid, a taxane, an HSP inhibitor, a Smoothened antagonist, a telomerase inhibitor, an anti-metastatic agent, an immunosuppressant, a biologic such as antibody or hormonal therapy.

Angiogenesis plays an important role in the progression of cancer and macular degeneration. This invention indicates that aurantiamide dipeptide compounds profoundly inhibit angiogenic functions of human early and late endothelial progenitor cells. The compounds also exhibits the promising anti-angiogenic effects both ex vivo and in vivo. Particularly, the compounds are novel angiogenesis inhibitors to block tumor growth and metastasis of melanoma as well as the pathological neovascularization of AMD.

EXAMPLES

Materials and Methods:

Isolation and Cultivation of Human CD34-Positive Endothelial Progenitor Cells

This investigation conforms with the principles outlined in the Declaration of Helsinki for use of human tissue. Ethical approval was granted by the Institutional Review Board of the Mackay Memorial Hospital, Taipei, Taiwan. Informed consent was obtained from healthy donors before the collection of peripheral blood (80 mL). The peripheral blood mononuclear cells (PBMCs) were fractionated from other blood components by centrifugation on Ficoll-Paque™ plus (GE Healthcare) according to the manufacturer's instructions. CD34-positive progenitor cells were obtained and cultured. In brief, the cells were isolated from PBMCs using CD34 MicroBead kit and MACSTM Cell Separation System (all from Miltenyi Biotec). CD34-positive EPCs were maintained in MV2 complete medium (PromoCell) consisting of endothelial basal medium, 20% fetal bovine serum, hEGF, VEGF, hFGF-B, IGF-1, ascorbic acid, and heparin. $1 \times 10^6$ cells/cm$^2$ were seeded on fibronectin-coated dish (BD Biosciences) and maintained in 37° C. incubator under a humidified 95% air and 5% $CO_2$ atmosphere.

Cell Proliferation Assay

EPCs ($5 \times 10^3$ cells/well) were seeded onto 96-well plates. After 24 h incubation, the culture medium was removed and cells were incubated with fresh MV2 complete medium containing 2% FBS for 48 h in the absence or presence of Fmoc-10a. Cells were incubated with MTT (0.5 mg/mL) for 2 h. Formazan crystal was lysed by dimethyl sulfoxide (DMSO) and absorbance was measured at 550 nm with ELISA-reader.

Cytotoxicity Assay

EPCs were treated with MV2 complete medium containing 2% FBS for 48 h in the absence or presence of Fmoc-10a. The percentage of LDH release was calculated from the ratio of LDH activity in the medium to LDH activity in the cell lysate after Fmoc-10a treatment.

Cell Migration Assay

EPCs ($5 \times 10^4$ cells/well) were seeded onto the upper chamber with MV2 complete medium, then incubated in the bottom chamber with MV2 complete medium containing 2% FBS with the indicated concentrations of Fmoc-10. After 16 h of treatment, cells on the upper side of the filters were mechanically removed, and those migrated on the lower side were fixed with 4% formaldehyde, then stained with 0.5% crystal violet for 10 min. Cell migration was quantified by counting the number of stained cells in 10 random fields with the inverted phase contrast microscope and photographed.

Capillary Tube Formation Assay

Matrigel (BD Biosciences, Bedford, Mass.), which was used to promote the differentiation of EPCs into a capillary tube-like structure, was added to 48-well plates. The Matrigel-coated 48-well plates were incubated at 37° C. for 30 min to allow for polymerization. After gel formation, EPCs ($6 \times 10^4$ cells) were seeded per well on the layer of polymerized Matrigel in MV2 complete medium containing 2% FBS with the indicated concentrations of Fmoc-10a, followed by incubation for 10-16 h at 37° C. Photomicrographs of capillary tube formation were taken with the inverted phase contrast microscope. Tube formation was quantified by measuring the long axis of each tube in 3 random fields per well by using Image-Pro Plus software.

Colony-Forming Assay

Isolated PBMCs are resuspended in MV2 complete medium. After 2 days, the nonadherent cells were collected and replated onto a fibronectin-coated 24-well plate. Five days later, the number of colony-forming units (CFUs) od early EPCs per well was counted.

Early EPC Chemotaxis Assay

The chemotactic motility of early EPCs was evaluated using a Transwell. The lower filter surface was coated with gelatin. Fmoc-10a in presence or absence of MV2 complete medium was placed in the lower wells. The chamber was incubated at 37° C. for 4 hours. Cells were fixed with cold methanol and stained with 0.5% crystal violet.

Aortic Ring Sprouting Assay

Aortas were harvested from 8- to 10-week-old Sprague-Dawley rats. Following a complete washing, the aortas were cut into 1 mm ring segments. The aortic rings were placed in the 48-well plates which were pre-coated with 130 µl Matrigel and polymerized at 37° C. The wells were subsequently overlaid with another 50 µl Matrigel for sealing. VEGF (20 ng/ml) with or without Fmoc-10a was then added to the well. The cultured medium was changed every 3 days. Sprouting endothelial cells were observed and photographed on day 8. The area of sprouting vessels was measured quantitatively by Image-Pro Plus software.

Directed in vivo Angiogenesis Assay (DIVAA)

Surgical silicone tubes were filled at 4° C. with Matrigel containing VEGF with or without Fmoc-10a. Then, the dorsal haunches of the anesthetized mice (C57BL/6 mice) were shaved and sterile prepped. A 5 mm cutaneous incision was made and a 10 mm deep subcutaneous pocket was created with a sterile hemostat. DIVAA tubes were incubated at 37° C. for 1 hour to allow gel formation and then implanted into the dorsal flank of mice. After 15 days, DIVAA tubes were taken and photographed. Neovessels were quantified by measuring the hemoglobin of the plug with the Drabkin method. All procedures involving animal experiment were approved by the Institutional Animal Care and Use Committee at Mackay Medical College.

Culture of Melanoma Cells

Mouse melanoma cell line (B16F10) was obtained from American Type Culture Collection (ATCC, Manassas, Va.) and cultured in DMEM containing 10% FBS, penicillin (100 units/ml), streptomycin (100 µg/ml), and L-glutamine (2 mM). Cells were maintained in humidified air containing 5% CO2 at 37° C.

Invasion Assay

The upper side of the filters was coated with Matrigel (BD Biosciences, Bedford, Mass.) at a concentration of 125 µg/cm². B16F10 cells (5×10⁴ cells/well) were seeded onto the upper chamber with serum-free medium, then incubated in the bottom chamber with culture medium containing 10% FBS in the absence or presence of Fmoc-10a. After 16 h of treatment, cells on the upper side of the filters were mechanically removed, and those migrated on the lower side were fixed with 4% formaldehyde, then stained with 0.5% crystal violet for 10 min. Finally, invaded cells were quantified by counting the number of stained cells in 10 random fields with the inverted phase contrast microscope and photographed.

VEGF ELISA Assay

B16F10 cells were treated with various concentrations of Fmoc-10a or vehicle for 24 hr, and then the supernatant was collected to examine the amount of vascular endothelial growth factor (VEGF) protein. VEGF mouse ELISA Kit (Novex, Invitrogen) was used according to the manufacturer's instructions.

Subcutaneous Xenograft Model

B16F10 cells (2×10⁶) in a volume of 100 µL were injected subcutaneously into the right flank of the C57BL/6 mice. After 9 days, when tumors reached 2 mm in diameter, the mice were randomly given vehicle or the indicated doses of Fmoc-10a daily by intraperitoneal injection. Tumor size and body weight were measured every day. The tumor volume was calculated according to the following formula: $V=(length \times width^2/2)$. In accordance with the Animal Ethics Committee, the experiments should be stopped when an unbearable situation appeared in animals.

Experimental Metastasis Model

B16F10 cells (2×10⁶) were slowly injected into the lateral tail vein of C57BL/6 mice to initiate tumor metastasis. Fmoc-10a (1.5 or 4.5 mg/kg) was intraperitoneally administered to mice every day from 3 days before tumor cell injection to 21 days after tumor cell injection (the day sacrificed).

Oxygen-Induced Retinopathy (OIR)

The mouse model of OIR has been widely used to induce retinal neovascularization in studies related to retinal ischaemic diseases, including AMD, and in studies evaluating the efficacy of antiangiogenic compounds. Briefly, BALB/c-nude mice at postnatal day (P7) are subjected to hyperoxia (75% oxygen) along with their nursing dam for 5 days (P12), and then to room air to produce retinal neovascularization. Neovascularization occurs upon return to normoxia and peaks at P17. All of the mice in the OR model were perfusion fixed via left ventricular puncture at the time of euthanasia, with 5 ml rhodamine-conjugated dextran. Then, angiography of retinal vasculature was performed and retinal whole mounts were prepared to score features of retinopathy.

Figure 1D:
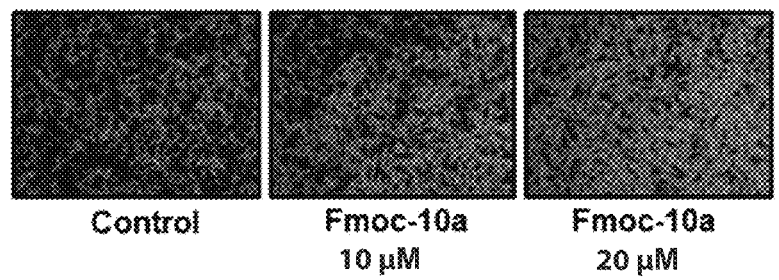
Figure 1E:
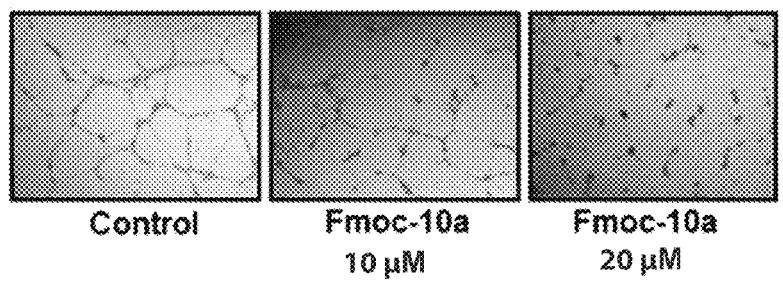

Example 1 Fmoc-10a Inhibits Cell Proliferation, Migration and Tube Formation of Human Late EPCs without Cytotoxic Effect After 48 h of treatment, Fmoc-10a suppresses cell proliferation of late EPCs in a concentration-dependent manner (FIGS. 1A&1B). In addition, Fmoc-10a does not induce LDH release of late EPCs even at high concentration (30 µM) (FIG. 1C). Fmoc-10a significantly inhibits cell migration and tube formation of late EPCs after 16 h treatment (FIGS. 1D&1E). These results indicate that Fmoc-10a has the ability to block in vitro angiogenesis without acting in a cytotoxic fashion.

Figure 2A:
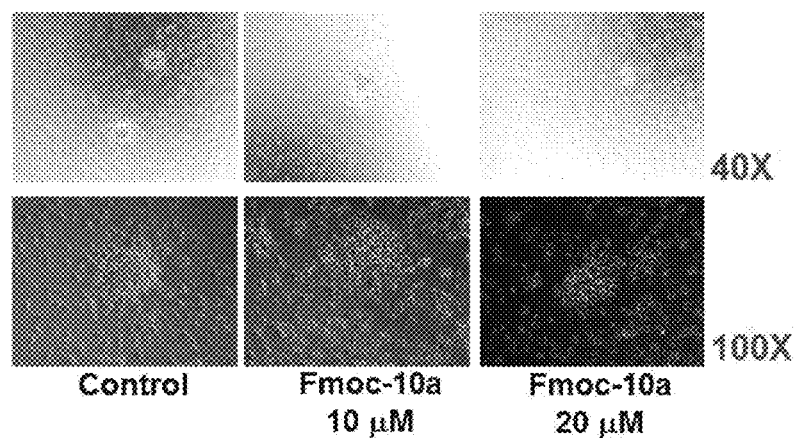
FIGS. 2A and 2B shows that Fmoc-10a inhibits the angiogenic potential of early EPCs.
Figure 2B:
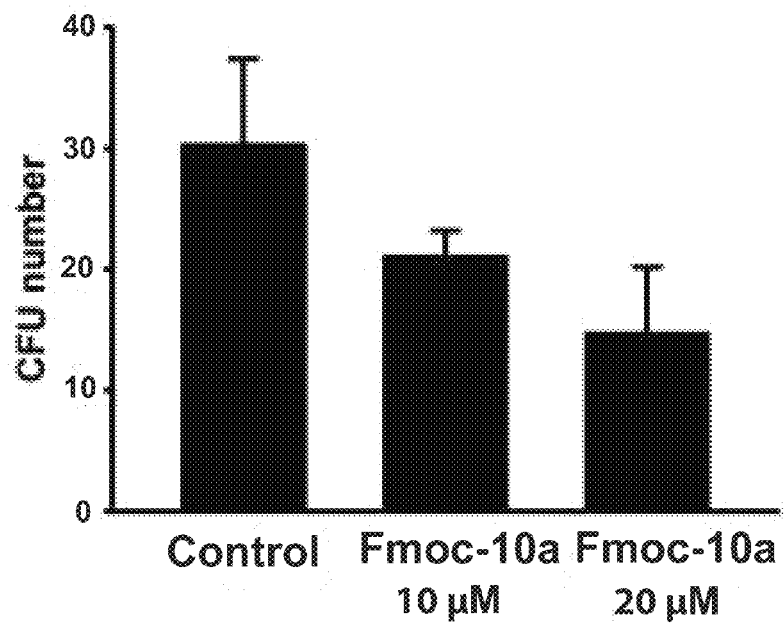

Example 2 Fmoc-10a Inhibits Colony Formation and Chemotactic Motility of Human Early EPCs Emerging evidences demonstrate that early EPCs promote angiogenesis and vasculogenesis by mediating the angiogenic switch. Fmoc-10a significantly inhibits CFU-Hill colonies and the elongated spindle-like cells at the periphery of early EPCs (FIGS. 2A&2B). Fmoc-10a also markedly suppresses chemotaxis of early EPCs (FIG. 2C). These results indicate that Fmoc-10a has the pharmacological function to block the angiogenic switch of early EPCs.

Example 3 Fmoc-10a Inhibits Angiogenesis Ex Vivo and In Vivo

Figure 3A:
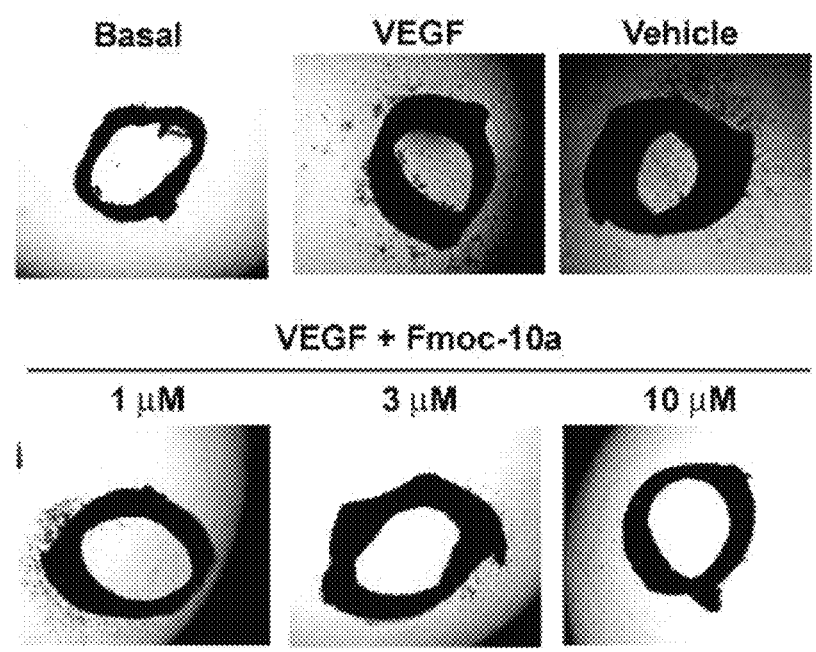
FIGS. 3A and 3B shows that Fmoc-10a inhibits angiogenesis ex vivo and in vivo.
Figure 3B:
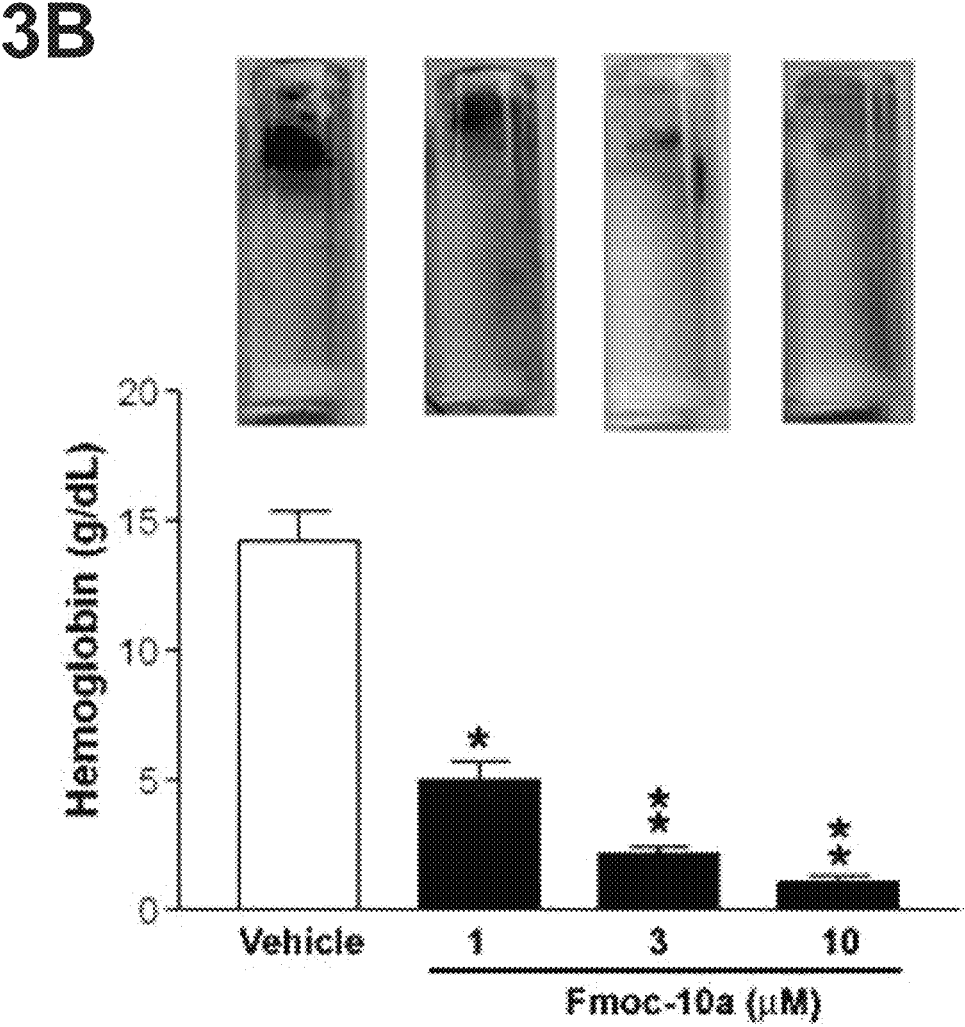

Vascular endothelial growth factor (VEGF) is the most potent angiogenic factor to regulate angiogenesis. Fmoc-10a dramatically abrogated VEGF-induced vessels sprouting from aortic rings (FIG. 3A). Furthermore, Fmoc-10a attenuated concentration-dependently microvessel formation in the Matrigel plugs by analyzing hemoglobin content. These results indicate that Fmoc-10a blocks VEGF-induced angiogenesis ex vivo and in vivo (FIG. 3B).

Figure 4A:
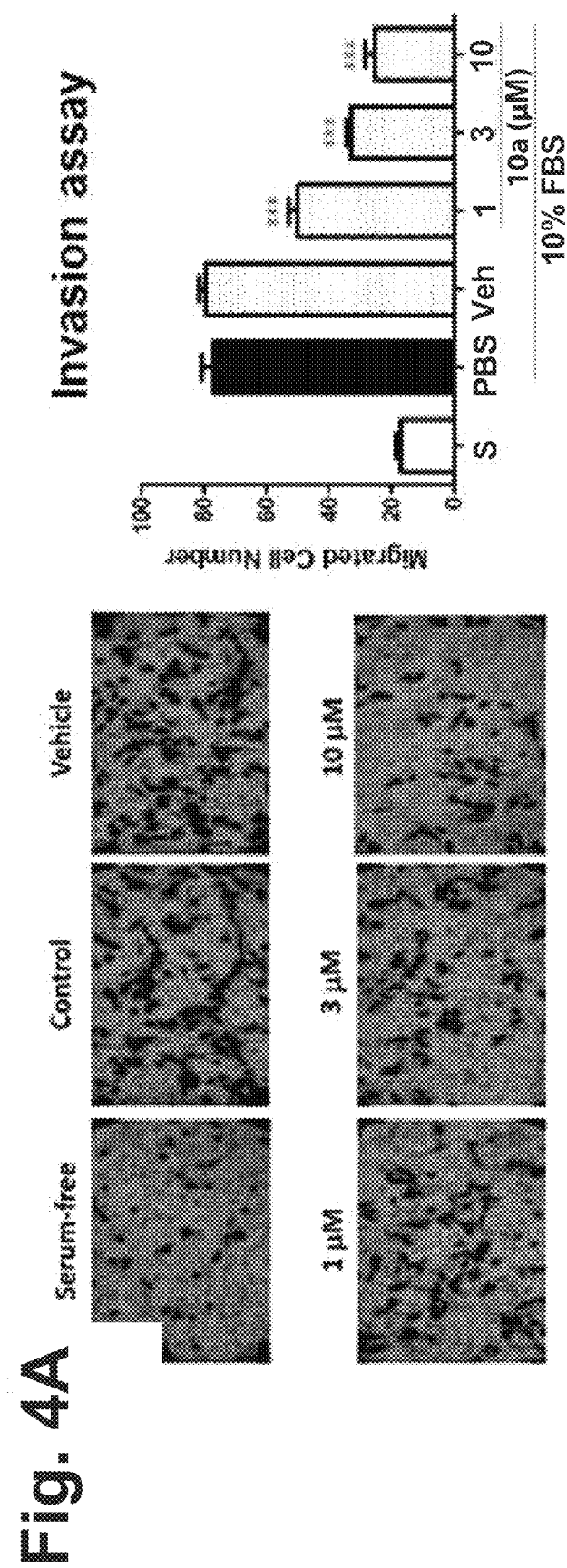
FIGS. 4A to 4D show that Fmoc-10a inhibits cell invasion, VEGF release, tumor growth and metastasis of melanoma cancer.
Figure 4B:
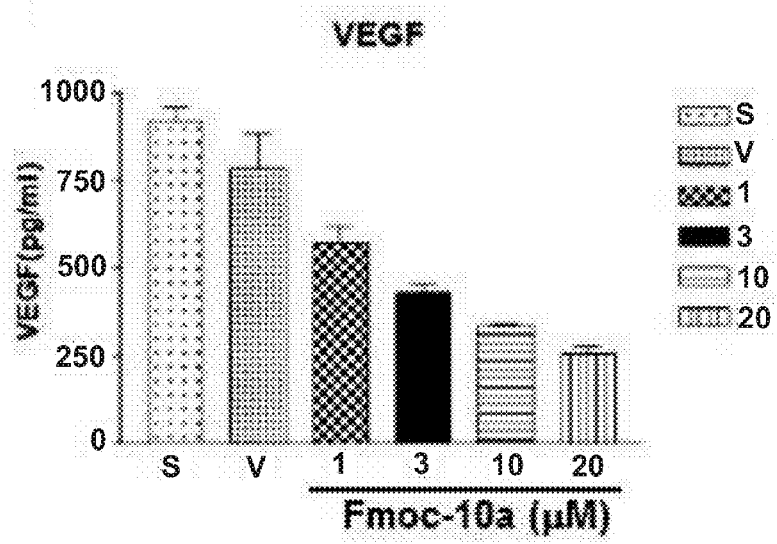
Figure 4C:
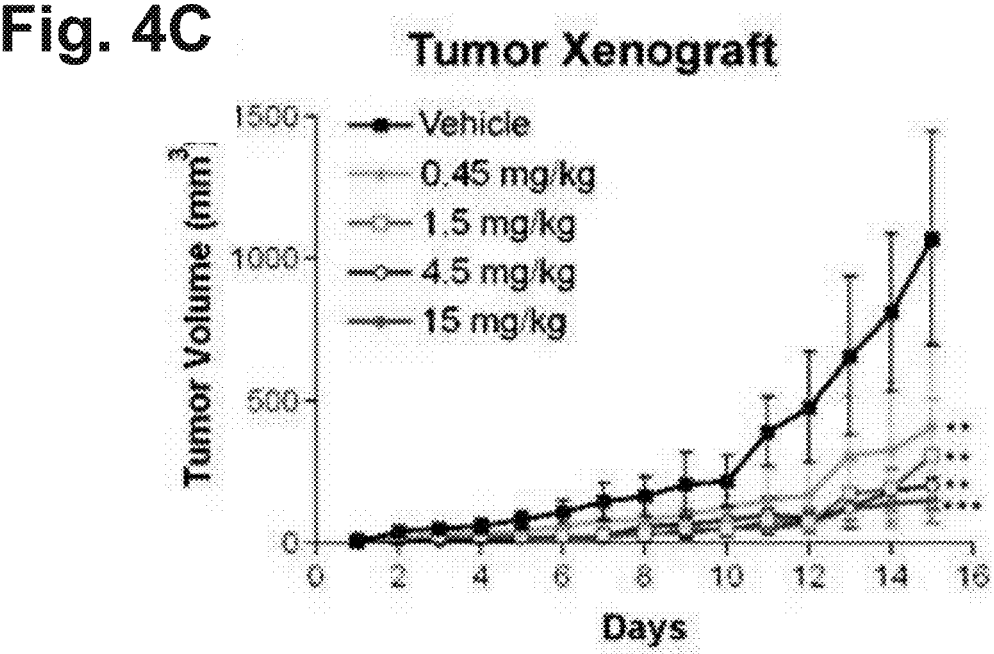
Figure 4D:
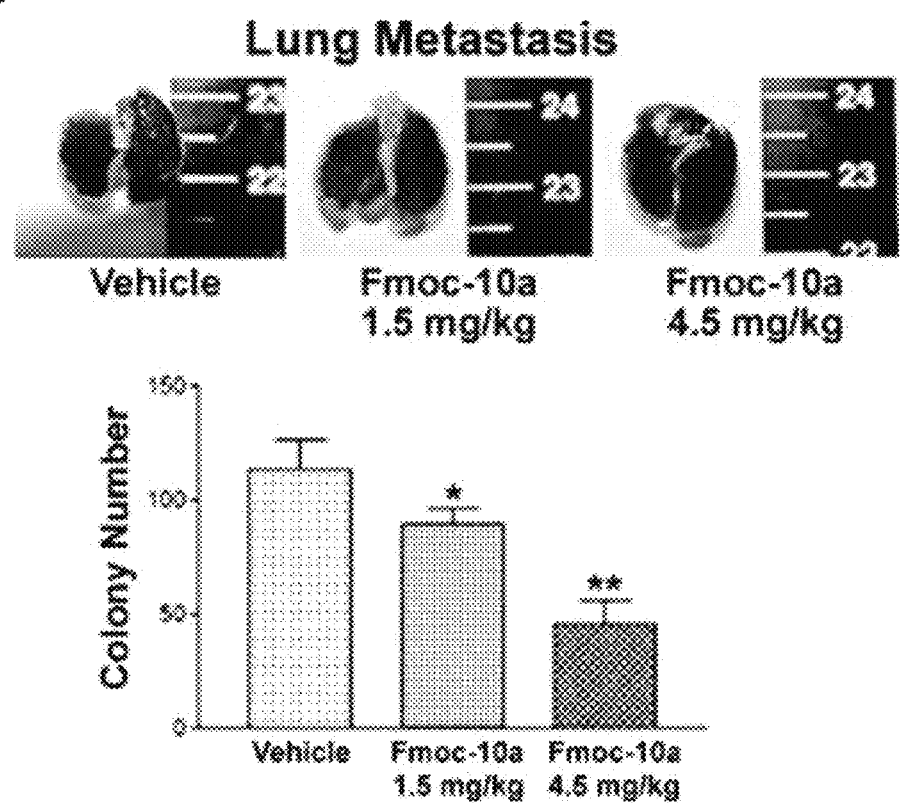

Example 4 Fmoc-10a Inhibits Tumor Growth and Metastasis of Melanoma In Vitro and Iv Vivo Melanoma is an aggressive skin cancer and also the almost skin cancer-related cause of death. Although melanoma is a relatively rare cancer, the notorious aggressiveness of melanoma is due to its remarkable metastatic propensity. Malignant melanoma has been well documented as a high angiogenic tumour type, clearly demonstrating new vessel formation as an important step in disease progression from atypical melanocytes. Angiogenic growth factor, such as VEGF, is overexpressed in melanoma and has been found to correlate with disease progression and prognosis. We demonstrate that Fmoc-10a significantly inhibits cell invasion and the production of VEGF in melanoma cells (FIGS. 4A&4B). Fmoc-10a potently blocks tumor growth of melanoma cells in a dose-dependent manner (FIG. 4C). Moreover, Fmoc-10a substantially suppresses lung metastasis of melanoma cancer (FIG. 4D). These results indicate that Fmoc-10a exhibits the novel anti-tumor and anti-metastasis activity through suppressing the production of VEGF and invasive property in melanoma cells, and the inhibition of angiogenesis in the melanoma microenvironment.

Figure 5B:
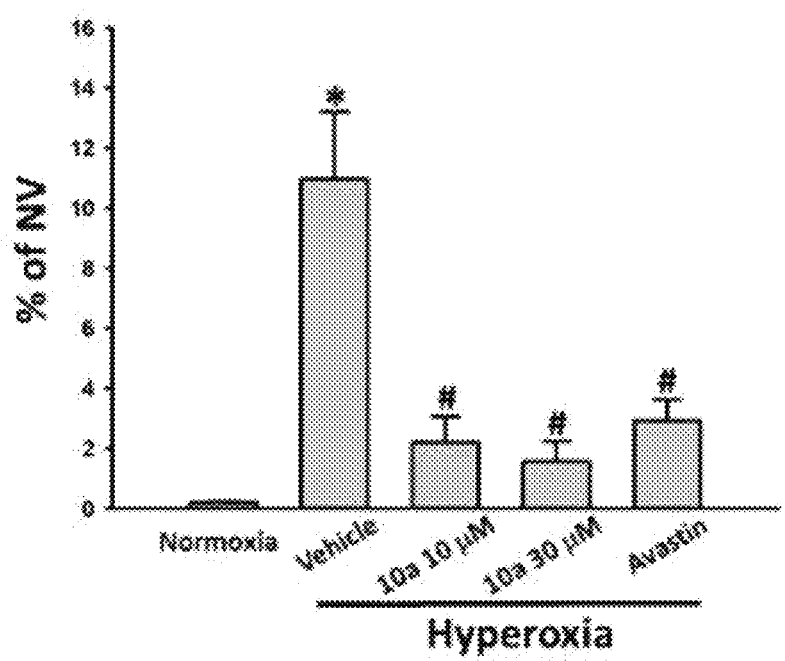
Figure 5B:
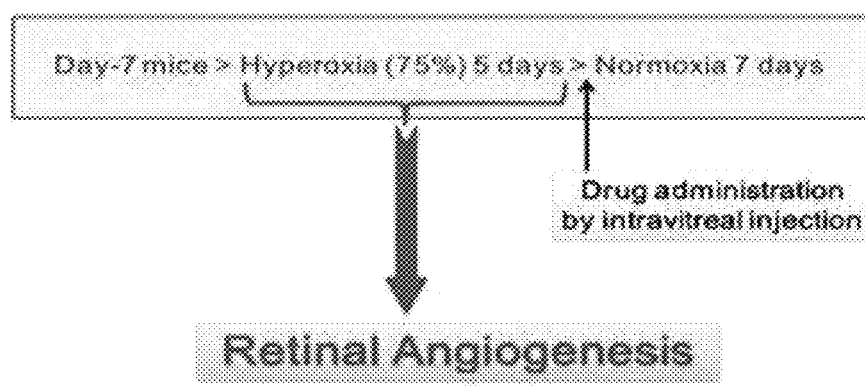

Example 5 Fmoc-10a Inhibits the Choroidal Neovascularization (CNV) in AMD Animal Model Neovascularization plays a critical role in AMD. The treatment of ocular neovascular diseases is being revolutionized by intravitreal therapies targeting VEGF. Fmoc-10a significantly blocks hyperoxia-induced pathological neovascularization in mice as Avastin (FIG. 5). These results indicate that Fmoc-10a is a promising angiogenesis inhibitor with the potential for treatment of angiogenesis-related diseases, such as AMD.

Targeting EPCs to block angiogenesis is currently attractive therapeutic approach for angiogenesis-related diseases. Herein, the inventors have shown that Fmoc-10a, an aurantiamide dipeptide compound, profoundly inhibits angiogenic functions of human early and late EPCs. Fmoc-10a also exhibits the promising anti-angiogenic effects both ex vivo and in vivo. Fmoc-10a is a novel angiogenesis inhibitor to block tumor growth and metastasis of melanoma as well as the pathological neovascularization of AMD. Therefore, the invention will have a great potential applied in the treatment of the angiogenesis-related diseases, especially melanoma cancer and AMD.

What is claimed is:

1. A method for ameliorating or treating ocular neovascularization, comprising administering an effective amount of a compound of the following Formula (I) to a subject,

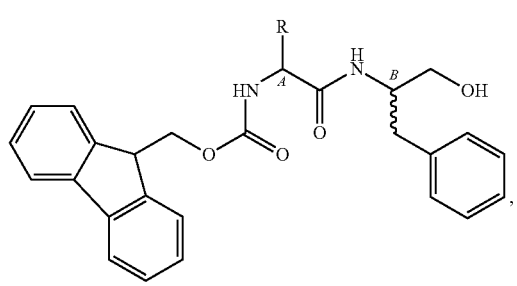

(I)

wherein R is —$(CH_2)_{1-4}$phenyl wherein phenyl is unsubstituted or substituted by one to three hydroxyl, $NH_2$, $NO_2$ or alkyl; —$(CH_2)_{1-4}$indolyl; —$(CH_2)_{1-4}$naphthalenyl; or isopropyl, or a tautomer, stereoisomer or enantiomer thereof, or a pharmaceutically acceptable salt thereof.

2. The method of claim 1, wherein R is —$CH_2$phenyl, —$CH_2$indolyl, —$CH_2$naphthalenyl or isopropyl.

3. The method of claim 1, wherein R is isopropyl.

4. The method of claim 1, wherein the compound of formula (I) is selected from:
(9H-Fluoren-9-yl)methyl(S)-1-((S)-1-hydroxy-3-phenylpropan-2-ylamino)-1-oxo-3-phenylpropan-2-ylcarbamate;
(9H-Fluoren-9-yl)methyl(S)-1-((R)-1-hydroxy-3-phenylpropan-2-ylamino)-1-oxo-3-phenylpropan-2-ylcarbamate;
(9H-Fluoren-9-yl)methyl(S)-1-((S)-1-hydroxy-3-phenylpropan-2-ylamino)-3-(1H-indol-3-yl)-1-oxopropan-2-ylcarbamate;
(9H-Fluoren-9-yl)methyl(S)-1-((R)-1-hydroxy-3-phenylpropan-2-ylamino)-3-(1H-indol-3-yl)-1-oxopropan-2-ylcarbamate;
(9H-Fluoren-9-yl)methyl(S)-1-((S)-1-hydroxy-3-phenylpropan-2-ylamino)-3-(naphthalen-2-yl)-1-oxopropan-2-ylcarbamate;
(9H-Fluoren-9-yl)methyl(S)-1-((R)-1-hydroxy-3-phenylpropan-2-ylamino)-3-(naphthalen-2-yl)-1-oxopropan-2-ylcarbamate;
(9H-Fluoren-9-yl)methyl(S)-1-((S)-1-hydroxy-3-phenylpropan-2-ylamino)-3-methyl-1-oxobutan-2-ylcarbamate; and
(9H-Fluoren-9-yl)methyl(S)-1-((R)-1-hydroxy-3-phenylpropan-2-ylamino)-3-methyl-1-oxobutan-2-ylcarbamate;
or a tautomer, stereoisomer or enantiomer thereof, or a solvate, prodrug or a pharmaceutically acceptable salt thereof.

5. The method of claim 1, wherein the compound is (9H-fluoren-9-yl)methyl(S)-1-((R)-1-hydroxy-3-phenylpropan-2-ylamino)-3-methyl-1-oxobutan-2-ylcarbamate,

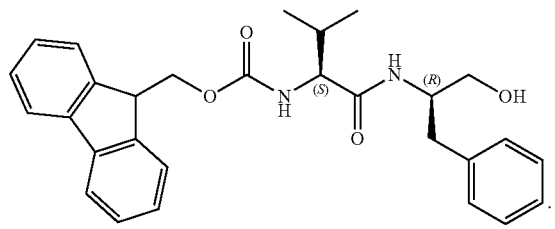

6. The method of claim 1, wherein the ocular neovascularization is macular degeneration.

7. The method of claim 6, wherein the macular degeneration is wet macular degeneration.

8. The method of claim 7, wherein the wet macular degeneration is age-related macular degeneration (AMD).

9. The method of claim 6, wherein the administration is in an intravitreal, intraocular or periocular route.

10. The method of claim 6, wherein the compound is formulated as an injection or eye drop.

* * * * *

UNITED STATES PATENT AND TRADEMARK OFFICE
CERTIFICATE OF CORRECTION

PATENT NO. : 9,872,882 B2
APPLICATION NO. : 14/981178
DATED : January 23, 2018
INVENTOR(S) : Hung-I Yeh et al.

It is certified that error appears in the above-identified patent and that said Letters Patent is hereby corrected as shown below:

On the Title Page

Item [73], Assignee corrected to read as follows:
MACKAY MEDICAL COLLEGE     NEW TAIPEI CITY, TAIWAN
MACKAY MEDICAL FOUNDATION THE PRESBYTERIAN CHURCH IN TAIWAN MACKAY MEMORIAL HOSPITAL     TAIPEI CITY, TAIWAN
CHANG GUNG UNIVERSITY     TAOYUAN CITY, TAIWAN Signed and Sealed this
Fifth Day of June, 2018

Andrei Iancu
*Director of the United States Patent and Trademark Office*